(12) United States Patent
Blackstone et al.

(10) Patent No.: US 8,912,122 B1
(45) Date of Patent: Dec. 16, 2014

(54) WETTING AGENT COMPOSITION FOR ENHANCING PLANT PRODUCTIVITY

(71) Applicants: Michael Blackstone, Jacksonville, FL (US); Nathan A. Welch, Pelzer, SC (US)

(72) Inventors: Michael Blackstone, Jacksonville, FL (US); Nathan A. Welch, Pelzer, SC (US)

( * ) Notice: Subject to any disclaimer, the term of this patent is extended or adjusted under 35 U.S.C. 154(b) by 0 days.

(21) Appl. No.: 14/086,455

(22) Filed: Nov. 21, 2013

(51) Int. Cl.
*A01N 25/26* (2006.01)
*A01N 59/04* (2006.01)
*A01N 25/00* (2006.01)
*A01N 37/00* (2006.01)
*A01N 25/10* (2006.01)
*C05G 3/02* (2006.01)
*C05G 3/06* (2006.01)

(52) U.S. Cl.
CPC ... *C05G 3/06* (2013.01); *C05G 3/02* (2013.01)
USPC ........ 504/100; 504/101; 504/116.1; 504/313; 504/360

(58) Field of Classification Search
None
See application file for complete search history.

(56) References Cited

U.S. PATENT DOCUMENTS

| | | |
|---|---|---|
| 2,716,058 A | 8/1955 | Rapson et al. |
| 2,999,045 A | 9/1961 | Mitchell et al. |
| 3,036,118 A | 5/1962 | Jackson et al. |
| 3,909,345 A | 9/1975 | Parker et al. |
| 4,426,254 A | 1/1984 | Wood et al. |
| 4,673,460 A | 6/1987 | Raff |
| 4,906,331 A | 3/1990 | Blackstone et al. |
| 4,952,277 A | 8/1990 | Chen et al. |
| 5,032,224 A | 7/1991 | Ahluwalia |
| 5,298,120 A * | 3/1994 | Blackstone ..................... 162/76 |
| 5,814,123 A | 9/1998 | Hansen |
| 5,865,869 A | 2/1999 | Hansen |
| 6,039,966 A | 3/2000 | Kostka et al. |
| 6,200,961 B1 | 3/2001 | Kostka et al. |
| 6,375,969 B1 | 4/2002 | Kostka et al. |
| 6,416,775 B1 | 7/2002 | Kostka et al. |
| 6,460,290 B1 | 10/2002 | Moore et al. |
| 6,826,866 B2 | 12/2004 | Moore et al. |
| 6,851,219 B2 | 2/2005 | Kostka et al. |
| 7,399,730 B2 | 7/2008 | Kostka et al. |
| 7,541,386 B2 | 6/2009 | Kostka et al. |
| 7,655,597 B1 | 2/2010 | Sanders |

OTHER PUBLICATIONS

Head-to-Head Challenge—Agrotain, Koch Agronomic Services, LLC (2011).
Aquatrols IrrigAid® Gold MSDS, Prepared May 7, 2010.
Koch Agrotain® Plus Nitrogen Stabilizer SDS, UK Version, Updated Mar. 22, 2012.
Koch Agrotain® Plus Nitrogen Stabilizer SDS, US Version, Updated Mar. 22, 2012.
SFP Avail® for Granular Phosphate Fertilizers, Prepared Jan. 16, 2012.

* cited by examiner

*Primary Examiner* — Alton Pryor
(74) *Attorney, Agent, or Firm* — Dority & Manning, P.A.

(57) ABSTRACT

The present invention is directed to a method for increasing the wetting rate of a plant growth medium utilizing a wetting agent composition. The composition is comprised of at least one modified block copolymer. The modified block copolymer is comprised of an ester of an ethylene oxide-propylene oxide block copolymer and a fatty acid. The composition of the present invention also enhances plant growth and productivity by increasing the water uptake and the nutrient uptake by the plant roots.

19 Claims, No Drawings

WETTING AGENT COMPOSITION FOR ENHANCING PLANT PRODUCTIVITY

BACKGROUND

Plants generate their food supply by converting carbon dioxide and water into sugars and starches during photosynthesis. Consequently, plant growth is dependent on receiving an adequate amount of light energy, carbon dioxide, and water, among other nutrients. Thus, in some instances, plant growth may be stunted when plants do not receive a sufficient amount of water. For instance, water may be lost when it evaporates from the plant growth medium or transpires from the leaves and stems of the plants. The moisture content in the plants and the surrounding plant growth medium can also be affected by the weather such as solar radiation, temperature, wind, and humidity. All of these factors may result in a plant growth medium, such as soil, with a low moisture content.

When the moisture content of the plant growth medium is low, further challenges are presented. For instance, a dry plant growth medium presents challenges for rewetting the plant medium because water is inhibited from infiltrating the medium. The upper surface of the dry medium is generally hard and almost impenetrable without manipulation. Even after manipulation, the dry medium must first be wetted before water is allowed to infiltrate and gain access to the plant roots.

Additionally, most plants obtain their nutritional requirements from the plant medium in which they grow. These nutrients include macronutrients such as nitrogen (N), phosphorus (P), potassium (K), calcium (Ca), magnesium (Mg), and sulfur (S) and micronutrients such as boron (B), chlorine (Cl), copper (Cu), iron (Fe), manganese (Mn), molybdenum (Mo), zinc (Zn), and nickel (Ni) which are generally provided from fertilizers. The nutrients are exchanged between the plant roots and the plant medium generally in the form of ions in the presence of water. Consequently, when the moisture in the plant growth medium is low, plants may be unable to grow because of an insufficient exchange of nutrients.

Compositions and methods have been suggested for enhancing the properties of the plant growth medium in order to enhance plant growth and productivity. U.S. Pat. No. 5,865,869 to Hansen is directed to a method for improving the watering of plant roots utilizing a composition comprising a humectant, a binder, water, and a wetting agent such as an octylphenol ethoxylate or a nonylphenol ethoxylate. U.S. Pat. Nos. 6,460,290 and 6,826,866 to Moore et al, are directed to water-soluble fertilizers containing an alkyl polyglycoside. U.S. Pat. No. 7,541,386 to Kostka et al. is directed to a composition consisting of an ethylene oxide-propylene oxide block copolymer having an HLB value of less than or equal to 2, an average molecular weight of greater than 3,000, and a percent hydrophile of less than or equal to 10 for increasing the wetting rate of water repellent soil.

While other methods and compositions have been utilized, the effectiveness has varied significantly. Consequently, there is a need for a composition that provides increased wetting rates and allows water to infiltrate the plant growth medium. Furthermore, there is a need for providing a composition that assists in improving the water uptake and the nutrient uptake by plant roots.

SUMMARY

In general, the present disclosure is directed to a method for increasing the wetting rate of a plant growth medium. The method comprises the step of contacting the plant growth medium with a wetting agent composition. The wetting agent composition is comprised of at least one modified block copolymer. The modified block copolymer is comprised of an ester of an ethylene oxide-propylene oxide block copolymer and a fatty acid.

The ethylene oxide-propylene oxide block copolymer is represented by the formula

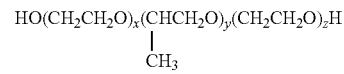

wherein x, y, and z are integers having a value of 1 or more. The ethylene oxide-propylene oxide block copolymer may have a molecular weight of from 500 g/mol to 30,000 g/mol. The ethylene oxide-propylene oxide block copolymer may have a hydrophile percent of from greater than 10% to less than 90%. The ethylene oxide-propylene oxide block copolymer may have an HLB value of from 3 to 30.

The fatty acid may have from 4 carbons to 22 carbons. The fatty acid may be selected from the group consisting of oleic acid, linoleic acid, adipic acid, abietic acid, maleic acid, and stearic acid. The fatty acid may be an unrefined fatty acid selected from the group consisting of coconut oil, cochin oil, corn oil, cottonseed oil, linseed oil, olive oil, palm oil, palm kernel oil, peanut oil, soybean oil, sunflower oil, tall oils, tallow, lesquerella oil, tung oil, whale oil, tea seed oil, sesame seed oil, safflower oil, rapeseed oil, fish oils, avocado oil, mustard oil, rice bran oil, almond oil, walnut oil, derivatives thereof, and combinations thereof. In one embodiment, the fatty acid is oleic acid.

According to one embodiment of the present invention, the composition may be comprised of a first modified block copolymer and a second modified block copolymer. The first modified block copolymer may be comprised of a first ethylene oxide-propylene oxide block copolymer. The first ethylene oxide-propylene oxide block copolymer may have a molecular weight of from 500 g/mol to 5,000 g/mol and a hydrophile percent of from greater than 10% to less than 40%. The second modified block copolymer may be comprised of a second ethylene oxide-propylene oxide block copolymer. The second ethylene oxide-propylene oxide block copolymer may have a molecular weight of from 7,500 g/mol to 20,000 g/mol and a hydrophile percent of from greater than 50% to less than 90%.

According to another embodiment of the present invention, a fertilizer may be applied to the plant growth medium. The fertilizer and the wetting agent composition may be applied contemporaneously.

According to another embodiment of the present invention, a pesticide may be applied to the plant growth medium. The pesticide and the wetting agent composition may be applied contemporaneously.

Other features and aspects of the present disclosure are discussed in greater detail below.

DETAILED DESCRIPTION

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations.

In general, the present invention is directed to a method for increasing the wetting rate of a plant growth medium. However, a person of ordinary skill in the art will understand that the present invention may also present additional benefits such as a method for increasing the water uptake by plant roots, a method for increasing the nitrogen uptake by plant roots, a method for increasing the potassium uptake by plant roots, a method for conserving water, and many others.

According to the present invention, the method comprises the step of contacting a plant growth medium with a wetting agent composition. The plant growth medium may be soil. The wetting agent composition is comprised of at least one modified block copolymer. The modified block copolymer may be an ester of an ethylene oxide-propylene oxide block copolymer and a fatty acid.

The block copolymers used in the composition are ethylene oxide-propylene oxide block copolymers. The ethylene oxide-propylene oxide block copolymers may be represented by the general formula:

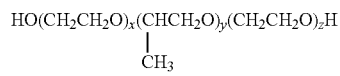

in which x, y, and z are integers having a value of 1 or more. It should be understood that any combination of x, y, and z may be utilized as long as the ethylene oxide-propylene oxide block copolymers have the desired molecular weight, HLB value, and hydrophile percent as defined herein. The ethylene oxide-propylene oxide block copolymers are generally described in U.S. Pat. No. 2,999,045 and U.S. Pat. No. 4,906,331, which are incorporated herein by reference in their entirety.

The ethylene oxide-propylene oxide block copolymers of the present invention may have an average molecular weight of at least about 500 g/mol, such as at least about 1,000 g/mol, such as at least about 2,000 g/mol, such as at least about 5,000 g/mol, such as at least about 7,500 g/mol, such as at least about 10,000 g/mol and generally less than about 30,000 g/mol, such as less than about 20,000 g/mol, such as less than about 15,000 g/mol, such as less than about 10,000 g/mol, such as less than about 5,000 g/mol, such as less than about 3,000 g/mol.

The hydrophilic-lipophilic balance (HLB) value is utilized to describe the hydrophilic or lipophilic tendencies of a surfactant molecule. Higher HLB values generally indicate a hydrophilic tendency while lower HLB values generally indicate a lipophilic tendency. The HLB value may also provide an indication of the solubility of a specific surfactant molecule. The ethylene oxide-propylene oxide block copolymers of the present invention may have an HLB value of greater than 2, such as greater than about 3, such as greater than about 4, such as greater than about 5, such as greater than about 10, such as greater than about 15, such as greater than about 20 and generally less than about 30, such as less than about 25, such as less than about 20, such as less than about 15, such as less than about 10, such as less than about 7. In one embodiment, the modified block copolymer of the present invention may exhibit nonionic surfactant like behavior.

In general, the ethylene oxide segments of the block copolymer exhibit hydrophilic tendencies. Thus, the ethylene oxide-propylene oxide block copolymers of the present invention may have a hydrophile percent greater than 10%, such as greater than about 15%, such as greater than about 20%, such as greater than about 40%, such as greater than about 50%, such as greater than about 60% and generally less than about 100%, such as less than about 90%, such as less than about 80%, such as less than about 50%, such as less than about 40%, based on the total number of propylene oxide and ethylene oxide monomer segments.

In general, the propylene oxide may be present in the block copolymers in an amount of greater than about 15%, such as greater than about 20%, such as greater than about 30%, such as greater than about 50%, such as greater than about 70% and less than about 100%, such as less than about 90%, such as less than about 85%, such as less than about 70%, such as less than about 50%, such as less than about 40%, based on the total number of propylene oxide and ethylene oxide monomer segments.

According to the present invention, the wetting agent composition is comprised of a modified block copolymer comprising an ester of an ethylene oxide-propylene oxide block copolymer and a fatty acid. Thus, the ethylene oxide-propylene oxide block copolymer is esterified with a fatty acid. In general, any fatty acid may be utilized for the esterification reaction with the ethylene oxide-propylene oxide block copolymer.

The fatty acid may be a saturated fatty acid or an unsaturated fatty acid. The fatty acid may have at least 4 carbon atoms, such as 8 carbon atoms, such as 12 carbon atoms, such as 15 carbon atoms and less than about 30 carbon atoms, such as less than about 25 carbon atoms, such as less than about 22 carbon atoms, such as 20 carbon atoms. The fatty acids utilized may include maleic acid, palmitic acid, stearic acid, adipic acid, abietic acid, linoleic acid, oleic acid, and the like, and any combination thereof.

However, unrefined fatty acids may also be utilized for the esterification reaction with the at least one ethylene oxide-propylene oxide block copolymer. These unrefined fatty acids include coconut oil, cochin oil, corn oil, cottonseed oil, linseed oil, olive oil, palm oil, palm kernel oil, peanut oil, soybean oil, sunflower oil, tall oils, tallow, lesquerella oil, tung oil, whale oil, tea seed oil, sesame seed oil, safflower oil, rapeseed oil, fish oils, avocado oil, mustard oil, rice bran oil, almond oil, walnut oil, derivatives thereof, and combinations thereof.

According to the present invention, the wetting agent composition is comprised of at least one ester of an ethylene oxide-propylene oxide block copolymer and a fatty acid. Therefore, an esterification reaction is conducted with a fatty acid and the an ethylene oxide-propylene oxide block copolymer.

The esterification process involves combining the ethylene oxide-propylene oxide block copolymer with a fatty acid in the presence of an acid catalyst. The mixing vessel is agitated under a nitrogen blanket during heating in the range of about 180° C. to about 220° C. Esterification is substantially complete when an acid value (mg KOH/g) of less than about 5.0 is obtained. However, it should be understood that other esterification process may be employed for producing the modified block copolymer. A person of ordinary skill in the art may utilize other esterification reactions to synthesize the ester of the fatty acid and the ethylene oxide-propylene oxide block copolymer since the invention described herein is not limited to a particular esterification method.

Upon synthesizing the modified block copolymer, the modified or esterified block copolymer may be dissolved in a solvent, such as water. The concentration of the modified block copolymer in the composition of the present invention that is contacted with the soil is not critical. The modified block copolymer may be initially present in the composition in an amount of at least about 1% by volume, such as at least about 5%) by volume, such as at least about 10% by volume, such as at least about 15% by volume, such as at least about 25% by volume and generally less than about 50% by volume, such as less than about 35% by volume, such as less than about 20% by volume, such as less than about 15% by volume, such as less than about 10% by volume, such as less than about 5% by volume.

The composition may be further diluted when applied to provide that the modified block copolymer is present in the composition in an amount of at least about 0.1% by volume, such as at least about 0.5% by volume, such as at least about 1% by volume, such as at least about 2% by volume, such as at least about 3% by volume, such as at least about 4% by volume and generally less than about 25% by volume, such as less than about 10% by volume, such as less than about 8% by volume, such as less than about 5% by volume, such as less than about 4% by volume.

According to one embodiment of the present invention, the wetting agent composition may include more than one modified block copolymer. Thus, the composition may include more than one ester of an ethylene oxide-propylene oxide block copolymer and a fatty acid. In such instances, the ethylene oxide-propylene oxide block copolymers may be the same or they may be different as long as they have the desired molecular weight, HLB value, and hydrophile percent as defined herein. Additionally, the fatty acid may be the same or different or long as the acid has the desired carbon atoms as defined herein.

For example, the composition may comprise a first modified block copolymer and a second modified block copolymer. The first modified block copolymer may be comprised of an ethylene oxide-propylene oxide block copolymer having a molecular weight of from about 1,000 g/mol to about 5,000 g/mol, such as from about 2,000 g/mol to about 4,000 g/mol and having a hydrophile percent of greater than 10% to less than about 35%, such as greater than about 15% to less than about 25%. The second modified block copolymer may be comprised of an ethylene oxide-propylene oxide block copolymer having a molecular weight of from about 10,000 g/mol to about 15,000 g/mol, such as from about 12,000 g/mol to about 14,000 g/mol and having a hydrophile percent of greater than about 60% to less than about 80%, such as greater than about 65% to less than about 75%.

Additionally, when more than one modified block copolymers are utilized, they may be present in the composition at the same concentration. Alternatively, they may be present in the composition at different concentrations. For instance, the first modified block copolymer may be present with the second modified block copolymer at a weight ratio of from about 10:1 to about 1:10, such as from about 5:1 to about 1:5, such as from about 2:1 to about 1:2, such as at about 1:1.

It should be understood that the combinations provided above are merely two combinations of modified block copolymers and ethylene oxide-propylene oxide block copolymers suitable according to the present invention. It should be understood that any ethylene oxide-propylene oxide block copolymers may be combined based on the molecular weight, HLB value, and hydrophile percent specifications provided herein.

Not to be limited by any specific theory, in general, the modified block copolymer comprising an ester of an ethylene oxide-propylene oxide block copolymer and a fatty acid may enhance plant growth and productivity because the modified block copolymer may behave like a wetting agent. A wetting agent is a compound that reduces the surface tension of a liquid which generally characterizes the tendency of the molecules of a liquid to bond together. For instance, cohesive forces are exerted between the liquid molecules holding them together. When the cohesive forces are strong, a liquid generally tends to form droplets on a surface. Adhesive forces are generally exerted between liquid molecules and an adjacent surface. When the adhesive forces are strong, a liquid generally tends to spread across the surface.

Thus, not to be limited by any specific theory, a wetting agent generally may stretch the bonds within the liquid and decrease the tendency of the molecules to bond together, which may allow the liquid to spread more easily across any solid surface. As such, the cohesive forces of the liquid are generally weakened and the adhesive forces of the liquid are generally strengthened. Consequently, because the modified block copolymer may exhibit behavior that exemplifies a wetting agent, it may assist in rewetting the plant growth medium (ie., soil) and the plant roots by allowing the water to spread more evenly across the surface (ie., surface of the soil or the plant roots). Additionally, by spreading more evenly across the surface, the contact area between the water and the surface may also be increased. Consequently, this may allow for a better uptake of water as well as other nutrients, such as nitrogen, potassium, phosphorus, and the like.

The composition of the present invention may also include other components and additives. For instance, the composition may also comprise anti-freezing agents, anti-foam agents, compatibility agents, oxidation and UV protectants, pH buffering agents, thickeners, binders, humectants, and combinations thereof.

The composition may include a fertilizer. The fertilizer may be a water-soluble fertilizer. The fertilizer may be a liquid fertilizer or a granular fertilizer. Suitable fertilizers are all known water-soluble inorganic and/or organic fertilizers, fertilizing salts, or mineral fertilizers, for example, urea, urea phosphate, ammonium nitrate, ammonium sulfate, mono- and di-ammonium phosphate, monopotassium phosphate, potassium chloride, potassium sulfate, potassium phosphate, potassium nitrate, ammonium sulfate-nitrate, potassium-ammonium phosphate, sodium nitrate, nitrogenous fertilizers, urea-containing mixed fertilizers, potassium salts, N, P, K-compound fertilizers, N, P, K-compound fertilizers containing trace elements and mixtures of such fertilizers or mineral fertilizers. A person of ordinary skill in the art will understand that the amount of fertilizer needed will depend on various factors such as the amount of nutrients required in the plant growth medium, the pH of the plant growth medium, and the like.

In one embodiment, the composition may include a fertilizer. However, it should also be understood that the fertilizer, such as a granular fertilizer, may be coated with the composition of the present invention. For instance, the wetting agent composition may be impregnated onto the granular fertilizer. The fertilizers may be coated with the wetting agent using any technique known in the art such as spraying, dripping, soaking, misting, and the like. As such, the wetting agent composition may be in contact with the soil or plant growth medium when coated on a granular fertilizer that is also in contact with the soil or plant growth medium.

The composition may include a biocide such as a pesticide. The pesticide may include fungicides, herbicides, insecticides, molluscicides, acaricides, or any combination thereof. Suitable pesticides include the following: acetanilides, benzoates, benzofurans, chlorinated hydrocarbons, hydroxybenzonitriles, imidazoles, nitroanilines, nitroxylenes, organophosphorous compounds, oxidazoles, phenoxy-phenoxy-alkane-carboxylic acid derivatives, pyrethroids, sulphates, triazoles, and the like. Suitable examples of each class of pesticides can be found in U.S. Pat. No. 6,039,966 to Kostka et al., which is incorporated herein by reference in its entirety. A person of ordinary skill in the art will understand that the amount of pesticide needed will depend on various factors such as the amount of area to be treated, the type of pests that need to be controlled, and the extent of pests that need to be controlled, and the like.

When the composition of the present invention also utilizes a fertilizer and/or a pesticide, the components can be combined using techniques known in the art to prepare a stable solution. For instance, the fertilizer and/or pesticide can be combined in the composition with the modified block copolymer. Alternatively, the fertilizer and/or pesticide can be solubilized as solutions in separate vessels or tanks, pumped, diluted if necessary and applied such that the fertilizer and/or pesticide solution and the wetting agent composition are applied contemporaneously. The solutions may also be applied immediately before or immediately after the wetting agent composition is applied to the plant growth medium. This approach may be utilized to minimize the effects of incompatibility among the components.

According to the present invention, the wetting agent composition is contacted with a plant growth medium such as soil. The wetting agent composition may be applied to a plant medium such as soil or a soil surface utilizing any method known in the art. The composition can be contacted with soil by directly applying the composition to soil surfaces, by utilizing aqueous irrigation delivery systems, or utilizing other methods known in the art. The composition can be applied utilizing sprayers such as book sprayers and backpack sprayers. In addition, the composition may also be directly applied to the main root areas of plants.

When applying the wetting agent composition, the watering rate will be at least about 0.1 mL/m$^2$, such as at least about 0.5 mL/m$^2$, such as at least about 1 mL/m$^2$, such as at least about 2 mL/m$^2$, such as at least about 5 mL/m$^2$ and generally less than about 100 mL/m$^2$, such as less than about 50 mL/m$^2$, such as less than about 25 mL/m$^2$, such as less than about 15 mL/m$^2$, such as less than about 10 mL/m$^2$, such as less than about 5 mllm$^2$. However, it should be understood that plants with larger root structures may require a higher watering rate while plants with smaller root structures such as grasses may require a lower watering rate. The concentrations that are applied to the plant growth media are not critical and can be adapted to the practical requirements in each case depending on the type of plants and the properties of the soil.

The wetting agent composition of the present invention may also be used to coat plant seeds or the outer covering or coating of plant seeds. When planted, the seed may be utilized to transport the modified block copolymer or surfactant into the plant growth medium in the presence of water. The composition and/or modified block copolymer can be applied to the seed using any technique known in the art. For instance, the coating can be created utilizing techniques such as spraying, dripping, soaking, misting, and the like. As such, the wetting agent composition may be in contact with the soil or plant growth medium when coated on a seed that is also in contact with the soil or plant growth medium.

The wetting agent composition and the method of the present invention present many advantages. For instance, the composition may provide an increased wetting rate resulting in a more effective wetting of the plant root zone and the plant growth medium. As such, the composition and method also improve the soil moisture content accessible to the plants and the plant roots, Consequently, the composition may also provide an increase in the uptake of water by the plant roots and/or an increase in the uptake of nutrients, such as nitrogen, by the plants roots. Consequently, because the water and/or nutrient uptake is increased, the composition and method of the present invention may also result in a reduction in the overall consumption of water for plant maintenance thereby conserving water and fertilizer/nutrients. The composition and method also improve the water and nutrient retention in the plant growth media. Consequently, because of the enhanced plant productivity, the reduction in the overall consumption of water, and the efficient uptake of water and nutrients, the method and composition of the present invention can also provide significant cost savings.

The present disclosure may be better understood with reference to the following examples.

EXAMPLE

The examples of the invention are given below by way of illustration and not by way of limitation. The following experiments were conducted in order to show some of the benefits and advantages of the present invention, Example 1

A composition of the present invention was produced according to the following method. Oleic acid esters were formed from ethylene oxide-propylene oxide block copolymers having the general formula

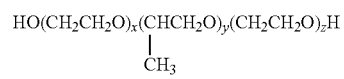

wherein x, y, and z are integers having a value of at least 1. For this particular Example 1, 45.23% by weight of an ethylene oxide-propylene oxide block copolymer sold by BASF under the name PLURONIC® F-127 and 45.23% of an ethylene oxide-propylene oxide block copolymer sold by BASF under the name PLURONIC® L-62 were combined into a mixing vessel with 9.39% by weight of oleic acid. P-toluene sulfonic acid in an amount of 0.15% was added as a catalyst to effect esterification. The mixing vessel was then heated and agitated under a nitrogen blanket at about 180° C. to about 220° C. until the acid value of the composition in mg KOH/g was less than 5.0. The esterification reaction yielded a modified block copolymer comprising an ethylene oxide-propylene oxide block copolymer esterified with an oleic acid.

Example 2

The composition of the present invention was tested to determine the ability of the composition to wet a plant growth medium and to determine the effect of the composition on nutrient uptake.

Four samples were prepared for analysis on four (4) individual half-acre (0.5) acre plots in a Fescue/Bermuda field. The Control Sample and Control Field did not include the wetting agent. Sample 1 applied to Field 1 was comprised of 3.75 volume % of the modified block copolymer. Sample 2 applied to Field 2 was comprised of 7.5 volume % of the modified block copolymer. Sample 3 applied to Field 3 was comprised of 11.25 volume % of the modified block copolymer. In each field, the wetting agent composition at the respective concentrations was applied at a rate 20 gallons/acre.

Prior to any application, tissues samples of the plants were taken from each field. The tissue samples were cut from three (3) one foot by one foot squares. After application of the wetting agents, tissue samples were taken once per week for one month. Each sample was taken from a random spot within the test field.

The results from the plant tissue analysis are shown in Table 1. These results indicate the change in nitrogen and phosphorus over the one month period.

| | Plant Tissue Analysis | |
|---|---|---|
| | % Change in Nitrogen | % Change in Phosphorus |
| Control Field | +2% | +12% |
| Field 1 | +24% | +43% |
| Field 2 | +38% | — |
| Field 3 | +8% | +29% |

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part.

Furthermore, those of ordinary skill in the art will appreciate that the foregoing description is by way of example only, and is not intended to limit the invention so further described in such appended claims.

The invention claimed is:

1. A method for increasing the wetting rate of a plant growth medium containing soil, the method comprising:
    contacting the plant growth medium with a wetting agent composition, the wetting agent composition comprising at least one modified block copolymer comprising an ester of an ethylene oxide-propylene oxide block copolymer and a fatty acid, wherein the ethylene oxide-propylene oxide block copolymer is represented by the formula

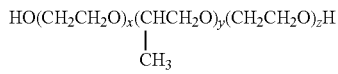

wherein x, y, and z are integers having a value of 1 or more.

2. The method of claim 1, wherein the ethylene oxide-propylene oxide block copolymer has a molecular weight of from about 500 g/mol to about 30,000 g/mol.

3. The method of claim 1, wherein the ethylene oxide-propylene oxide block copolymer has a hydrophile percent of from greater than 10% to less than about 90%.

4. The method of claim 1, wherein the ethylene oxide-propylene oxide block copolymer has an HLB value of from about 3 to about 30.

5. The method of claim 1, wherein the fatty acid has from 4 carbon atoms to 22 carbons atoms.

6. The method of claim 1, wherein the fatty acid is an oleic acid.

7. The method of claim 1, wherein the fatty acid is selected from the group consisting of linoleic acid, adipic acid, abietic acid, maleic acid, and stearic acid.

8. The method of claim 1, wherein the fatty acid is an unrefined fatty acid, the unrefined fatty acid selected from the group consisting of coconut oil, cochin oil, corn oil, cottonseed oil, linseed oil, olive oil, palm oil, palm kernel oil, peanut oil, soybean oil, sunflower oil, tall oils, tallow, lesquerella oil, tung oil, whale oil, tea seed oil, sesame seed oil, safflower oil, rapeseed oil, fish oils, avocado oil, mustard oil, rice bran oil, almond oil, walnut oil, derivatives thereof, and combinations thereof.

9. The method of claim 1, wherein the modified block copolymer is present in the composition in an amount of from 0.5% to 50% by volume.

10. The method of claim 1, wherein the composition comprises
    a first modified block copolymer, the first modified block copolymer comprising a first ethylene oxide-propylene oxide block copolymer, the first ethylene oxide-propylene oxide block copolymer having a molecular weight of from about 500 g/mol to about 5,000 g/mol and a hydrophile percent of from greater than 10% to less than about 40%,
    a second modified block copolymer, the second modified block copolymer comprising a second ethylene oxide-propylene oxide block copolymer, the second ethylene oxide-propylene oxide block copolymer having a molecular weight of from about 7,500 g/mol to about 20,000 g/mol and a hydrophile percent of from greater than about 50% to less than about 90%.

11. The method of claim 1, wherein the composition comprises a first modified block copolymer and a second modified block copolymer, the first modified block copolymer and the second modified block copolymer being present in the composition at a weight ratio of from about 10:1 to about 1:10.

12. The method of claim 1, further comprising
    applying a fertilizer to the plant growth medium,
    wherein the water-soluble fertilizer and the wetting agent composition are applied contemporaneously.

13. The method of claim 1, further comprising
    applying a pesticide to the plant growth medium,
    wherein the pesticide and the wetting agent composition are applied contemporaneously.

14. The method of claim 1, wherein the composition further comprises a fertilizer, a pesticide, or a combination thereof.

15. The method of claim 1, wherein the wetting agent composition is applied in an amount of from about 0.1 mL/m² to about 50 mL/m².

16. The method of claim 1, further comprising
    introducing the wetting agent composition to a main root area of a plant root.

17. The method of claim 1, wherein the wetting agent composition is coated on a granular fertilizer and wherein the granular fertilizer is in contact with the plant growth medium.

18. The method of claim 1, wherein the wetting agent composition is coated on a seed and wherein the seed is in contact with the plant growth medium.

19. A method for increasing the wetting rate of a plant growth medium containing soil, the method comprising:
    contacting the plant growth medium with a wetting agent composition, the wetting agent composition comprising at least one modified block copolymer comprising an ester of an ethylene oxide-propylene oxide block copolymer and a fatty acid,
    wherein the ethylene oxide-propylene oxide block copolymer is represented by the formula $$HO(CH_2CH_2O)_x(CHCH_2O)_y(CH_2CH_2O)_zH$$
$$|$$
$$CH_3$$

wherein x, y, and z are integers having a value of 1 or more,
wherein the ethylene oxide-propylene oxide block copolymer has a hydrophile percent of from greater than 10% to less than about 90%, and
wherein the ethylene oxide-propylene oxide block copolymer has an HLB value of from about 3 to about 30.

\* \* \* \* \*